(12) United States Patent
Keith et al.

(10) Patent No.: US 6,841,214 B1
(45) Date of Patent: Jan. 11, 2005

(54) VARIABLE STIFFNESS MICROTUBING AND METHODS OF MANUFACTURE

(75) Inventors: Lane A. Keith, Chattanooga, TN (US); Gary G. Massengale, Trenton, GA (US); John T. Riddle, Trenton, GA (US); Ronald B. Roth, Signal Mountain, TN (US)

(73) Assignee: MedSource Trenton, Inc., Trenton, GA (US)

( * ) Notice: Subject to any disclaimer, the term of this patent is extended or adjusted under 35 U.S.C. 154(b) by 0 days.

(21) Appl. No.: 08/480,411

(22) Filed: Jun. 7, 1995

Related U.S. Application Data

(63) Continuation-in-part of application No. 08/331,280, filed on Oct. 28, 1994, now Pat. No. 6,616,996.

(51) Int. Cl.[7] .............................................. B32B 1/08
(52) U.S. Cl. ..................... 428/35.8; 428/35.9; 428/36.2; 428/36.3; 428/36.91
(58) Field of Search ............................... 428/35.8, 35.9, 428/36.2, 36.3, 36.91, 189, 190, 156, 201, 220

(56) References Cited

U.S. PATENT DOCUMENTS

| 3,965,909 A | * | 6/1976 | Waddell et al. |
| 4,702,252 A | * | 10/1987 | Brooks et al. |
| 4,925,710 A | | 5/1990 | Buck et al. ................. 428/34.5 |

FOREIGN PATENT DOCUMENTS

| WO | 9320881 | * | 10/1993 |

* cited by examiner

*Primary Examiner*—Elizabeth M. Cole
(74) *Attorney, Agent, or Firm*—Miller & Martin PLLC

(57) ABSTRACT

A novel composite microtubing with variable stiffness over the length of the tubing and continuous process for manufacturing the same is provided. By removing portions of one or more selected layers of the composite microtubing, varying the pick count of a braided layer, and changing the diameter over the length of the microtubing, the stiffness of the microtubing may be varied by a factor of 100 from proximal end to distal end. The continuous process allows a predetermined stiffness pattern to be repeated over a measured length for economical manufacture and results, if desired, in tubing of extremely small diameter and extremely thin tube walls.

23 Claims, 4 Drawing Sheets

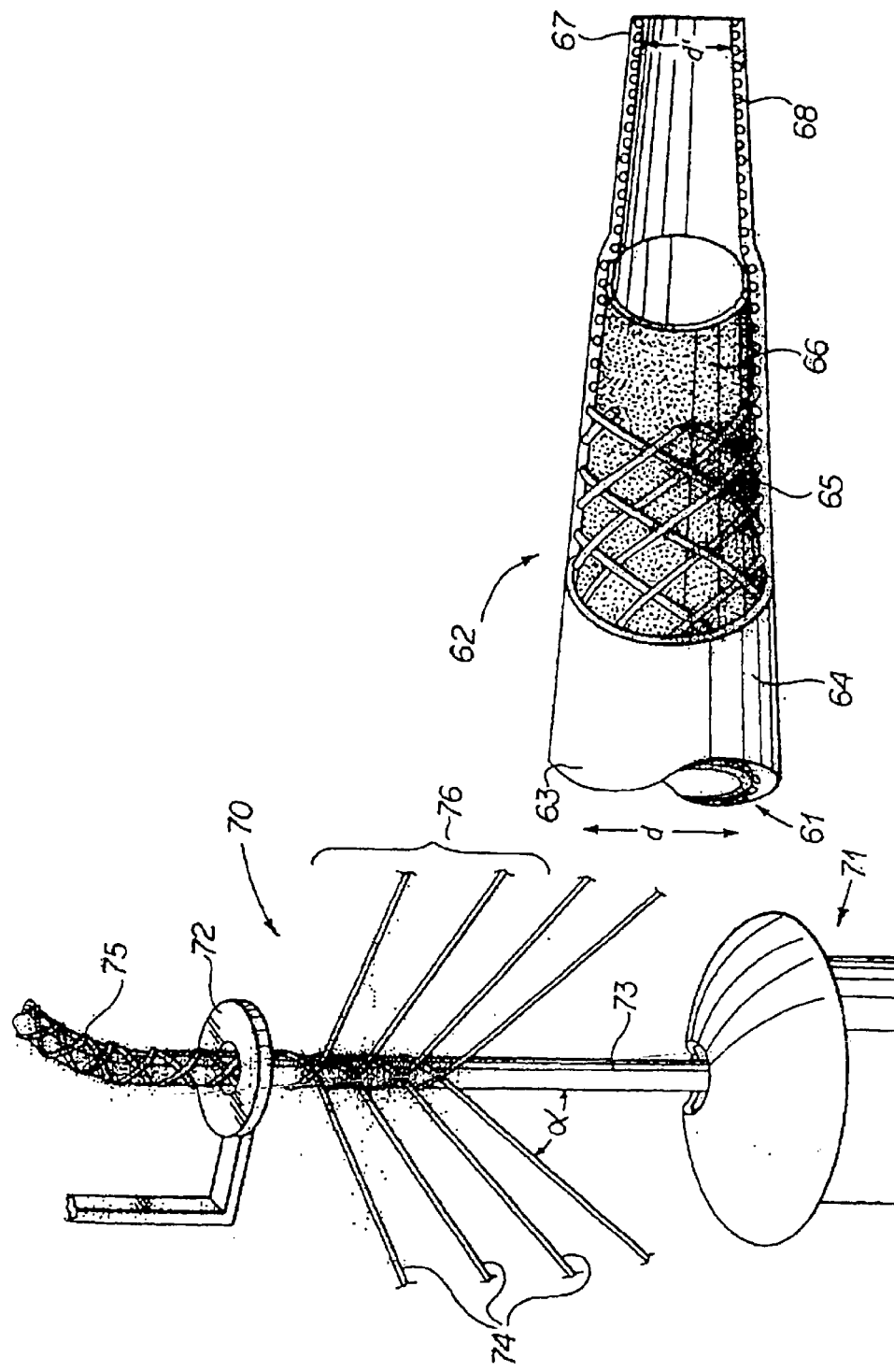

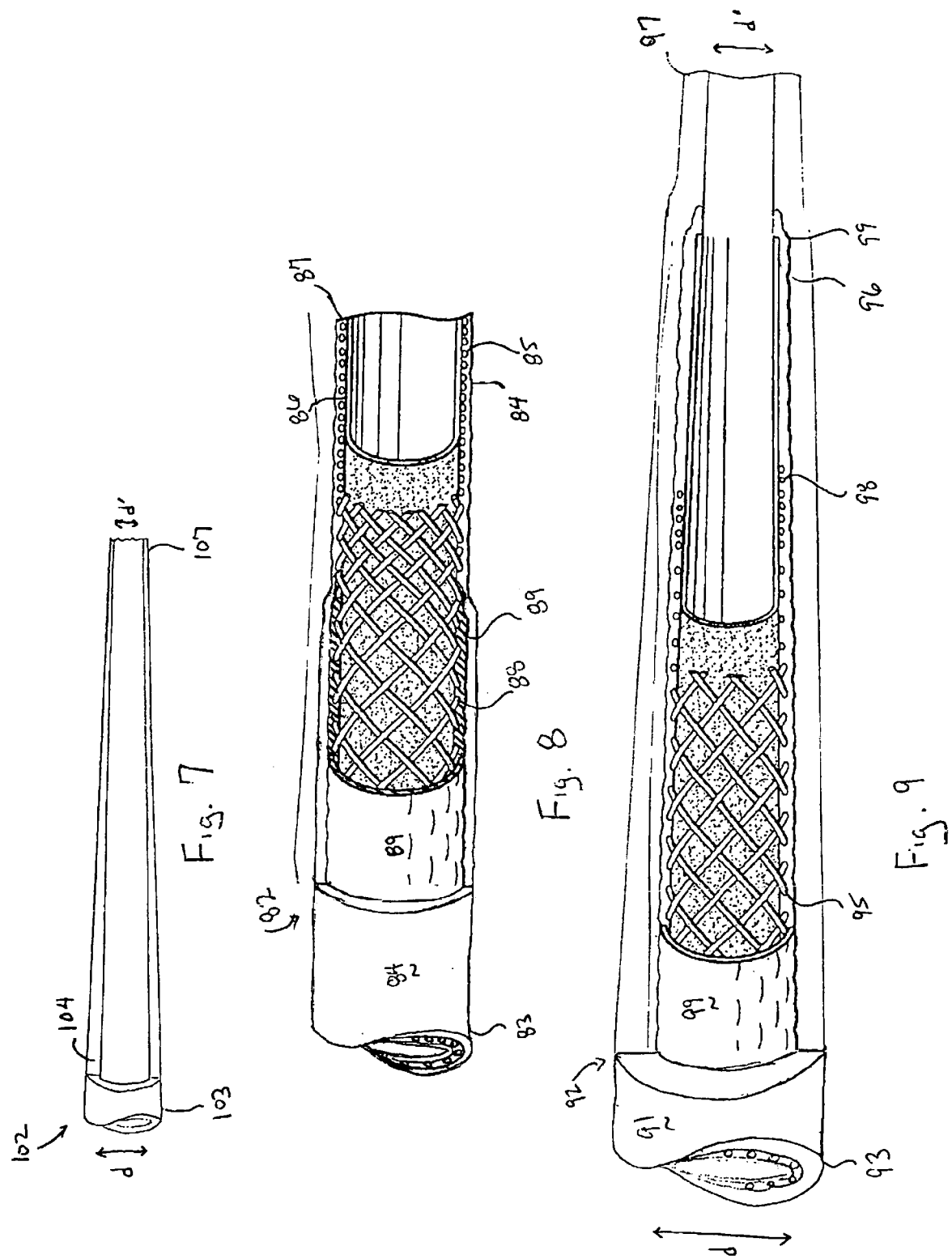

VARIABLE STIFFNESS MICROTUBING AND METHODS OF MANUFACTURE

This application is a continuation-in-part of application Ser. No. 08/331,280 filed Oct. 28, 1994, now U.S. Pat. No. 6,616,996.

The present invention relates to microtubing and more particularly to microtubing of variable stiffness over the length of the tubing. The microtubes of the present invention are typically manufactured at least partially of cured resin and are of outer diameter less than 0.225 inches (5.715 mm). The microtubes of this invention may usefully be employed in a variety of applications such as medical catheters for various diagnostic and therapeutic purposes.

BACKGROUND OF THE INVENTION

Fine gauge microtubing has been made for many years by coating a surface treated copper mandrel wire with one or more suitable curable resins and subsequently removing the mandrel wire after the resin coating has been cured. In this regard, attention is directed to U.S. Pat. No. 4,051,284 issued to Ohkubo, et al. on Sep. 27, 1977, and entitled "Method for Producing Heat Resistant Synthetic Resin Tubes," the entire content of this prior U.S. Patent being expressly incorporated by reference.

In medical applications, such as guide catheters, it is usually desirable that the hollow tube or microtube portion of the catheter have characteristics which vary over the length of the tube. Characteristics that are particularly desirable along various portions of catheter tubes include torque transmission or pushability, stiffness or flexibility, burst strength, and kink resistance. It is also necessary that the components of microtubes used in catheters be biocompatible so as not to induce thrombosis or other trauma when used.

SUMMARY OF THE INVENTION

The present invention comprises a novel multi-layer resin cured microtube and even single layer resin cured microtubes which vary in flexibility over their length. Resin cured layers of the microtube are generally comprised of polyimides, fluoropolymers, polyethylenes, NYLON, urethanes and polyurethanes, and such layers may be interspersed with one or more layers of coiled or braided metal wire or ribbon, or fibers, such as particularly glass, plastic or aramid fibers. The novel microtubes are manufactured according to a continuous process and selected layers or portions of layers may be removed by grinding or etching portions of the tubes. In addition, the number of braid picks per inch and the diameter of the tubing may vary along portions of the tube. By varying the materials comprising the layers of the microtubes, and in some instances the thickness of those layers, together with the braid pick count and microtubing diameter and shape, as well as selectively removing portions of resin or braid layers, it is possible to achieve variations in tubing stiffness on the order of over 100 to 1. In other words, for a given length of microtube, the proximal end may be over 100 times stiffer than the distal end. To obtain such wide variations in stiffness previously it has been necessary to fabricate tubing from separate tubing components. Such fabrication is not only time consuming and expensive, but the joints between tubing components are especially likely to fail or be prone to kinking.

In preferred embodiments of the present invention, the composite microtubes have wall thicknesses of about 0.0025 inches (0.0635 mm) to about 0.01 inches (0.254 mm), inner diameters of 0.005 inches (0.127 mm) or even less to about 0.2 inches (5.08 mm), and outer diameters of 0.01 inches (0.254 mm) to 0.22 inches (5.588 mm). Braid pick counts per inch may range from as few as 30 to 45 picks/inch up to as many as 280 picks/inch. The inner diameter of the microtubing may also vary so that the widest diameter is as much as twice the size as the narrowest diameter. When the layers, braid pick count, or diameter of the composite microtubing are varied, such variations preferably take place gradually over a length of approximately 1 inch or more to reduce the likelihood of kinking in the microtubing.

BRIEF DESCRIPTION OF THE DRAWINGS

FIG. 5 is an enlarged partial side sectional view of a length of tapered microtubing according to the present invention in which both the materials and the pick count of braiding are varied over distance.

FIG. 6 is an illustration of the braiding area of a braiding machine showing the guides which can be used when the pick count is varied.

FIG. 7 is an enlarged partial side section view of a single layer resin cured microtube according to the present invention.

FIG. 8 is an enlarged partial side sectional view of a composite microtube according to the present invention in which the material encapsulating the braid is changed over the length of the tube.

FIG. 9 is an enlarged partial side sectional view of a tapered composite microtube according to the present invention with an extruded outer layer.

DETAILED DESCRIPTION OF THE DRAWINGS

Figure 1:
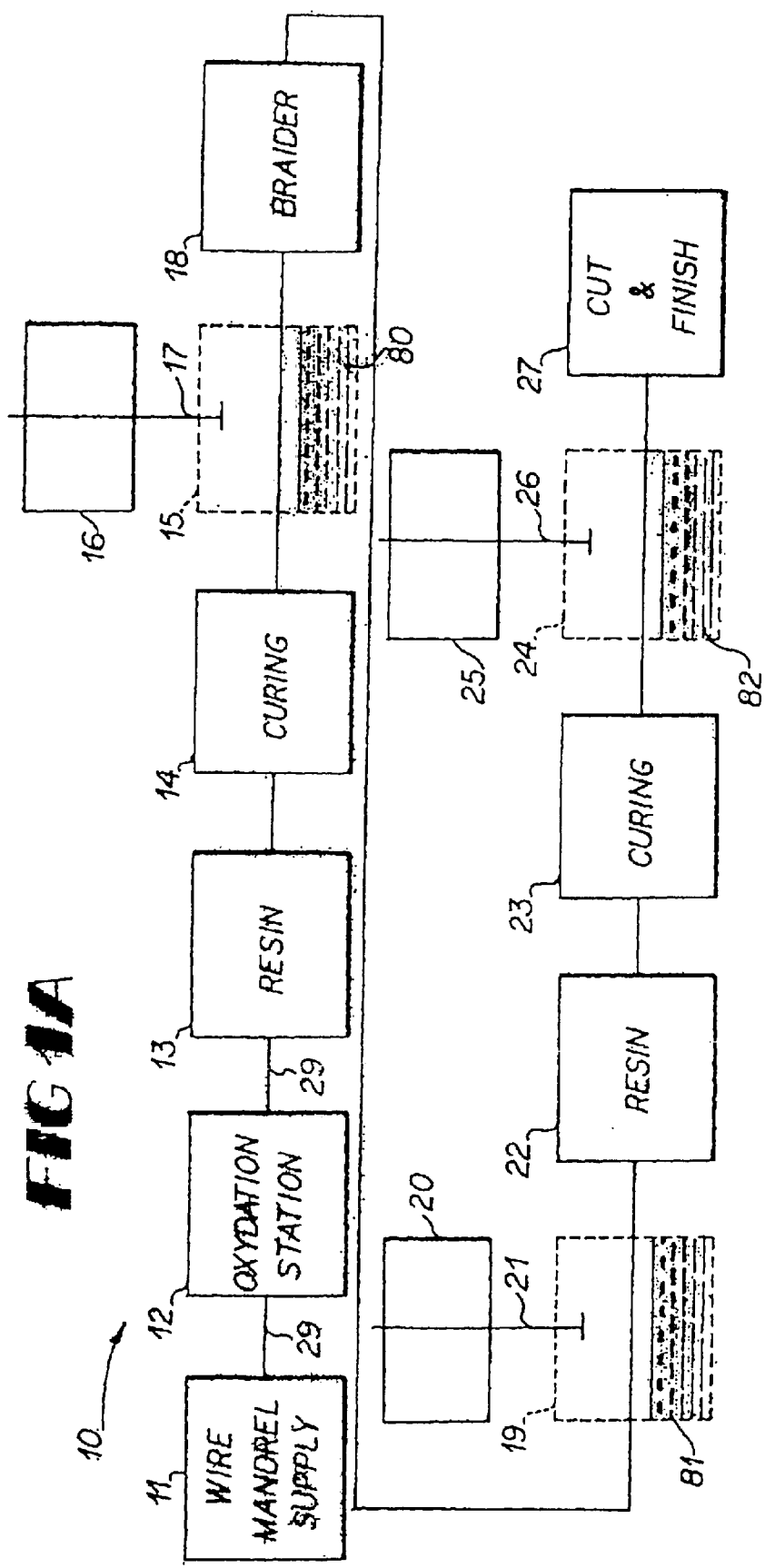
FIG. 1A is a flow diagram representing the steps employed in manufacturing microtubing in accordance with the teachings of the present invention.
FIG. 1B is a side elevation view of a section of standard wire mandrel.
FIG. 1C is a side elevation view of a section of tapered wire mandrel.

In FIG. 1, flow diagram 10 shows in graphic form the various steps employed in manufacturing the novel composite microtubing of the present invention. A wire mandrel 29 is supplied from wire mandrel supply 11 to an oxidation station 12 which will typically oxidize the outer surface of the wire mandrel 29 by a heat or chemically induced reaction. The oxidation allows mandrel 29 to be easily removed after layers of resin and/or braid materials have been formed on the mandrel 29. In lieu of an oxidized mandrel, which typically is a copper wire, it is also possible to use some wire mandrels in an unoxidized state such as silver plated copper wire or annealed stainless steel wire. The oxidized wire mandrel 29 then proceeds through a first resin bath 13 preferably of heat resistant synthetic varnish such as polyimide, polyamideimide, polyesterimide, polyesteramideimide, or a fluoropolymer. Preferred commercially available resins include the PYRE ML-5019 series of polyimide varnishes, the polyamic acid solutions of P.D. George Chemical Company of St. Louis, polytetrafluoroethylene (PTFE) and fluorinated ethylene propylene (FEP). PTFE or FEP fluoropolymers are typically used to provide a lower friction interior or exterior surface for the resulting microtubing. Although usually used for outer layers, polyurethane varnishes may also be used. The preferred polyurethanes are TECOFLEX solvent grade polyurethanes from Thermetics.

After the resin coated wire mandrel 29 is heat cured in curing oven 14, it may optionally be spooled or stored before further processing. The resin coated wire mandrel 29 may also optionally proceed across an etching solution 80 such as illustrated in tank 15. Controller 16 will selectively raise and lower dipping roller 17 to submerge a portion of the resin coated wire mandrel 29 in the etching solution 80. For a polyimide resin, the etching solution 80 would typically comprise a heated strong base solution with pH of about 14, such as a sodium hydroxide solution, a strong heated acid with pH of about 1, or 956 ML Stripper available from Fidelity Chemical Company or equivalents. A less desirable alternative to etching is to mechanically remove a portion of the unused resin layer, as by centerless grinding. Centerless grinding is usually only acceptable for tubing with relatively thick walls such as would be formed by an extrusion process. If a TEFLON resin is used, it may be treated with Poly Etch™, available from Matheson Gas, which does not remove the cured TEFLON but does improve the adhesion of subsequent layers of polyimide resin. The FEP and PTFE resins, as well as polyethelyne resins are generally unsuitable for selective removal by etching.

It should be made clear that multiple layers of the same or different resins may be placed on the wire mandrel 29 by drawing the resin coated mandrel 29 through additional resin baths, curing ovens, and optionally across etching tanks. The next process step is to pass the resin coated wire mandrel 29 through a braider 18 such as a STEEGER braider machine, available from Wilhelm Steeger GmbH. To provide maximum variability it is desirable that the braider 18 be programmable to vary the capstan and carrier speeds and guide locations in accordance with a predetermined pattern, and as explained in greater detail in connection with FIG. 6.

The braider 18 typically utilizes between 8 and 32 strands of metal ribbon having a thickness between 0.0003 inches (0.000762 mm) and 0.003 inches (0.00762 mm) and a width between 0.0025 inches (0.00635 mm) and 0.01 inches (0.0254 mm), or alternatively round, D shaped, or other wire with diameter between 0.001 inches (0.00254 mm) and 0.004 inches (0.01016 mm). In other instances, fibers, most typically glass, plastic or aramid fibers such as KEVLAR may be used as a braiding material. The number of strands braided around the resin coated mandrel 29 is typically 16, but that number would often be reduced if the diameter of the mandrel 29 was 0.02 inches (0.0508 mm) or less. Similarly, more than 16 strands might be used if the mandrel were of diameter 0.1 inches (0.254 mm) or more. Typically, braiding will involve one strand of braid wire to a carrier on the braiding machine but it is possible to thread a single carrier with two or more wires for different braiding characteristics.

It should be understood at this point that in some cases in lieu of braiding, the resin coated mandrel 29 may simply be coiled with wire, ribbon, or fiber to achieve similar results. Braiding is generally preferred, however. Braiding or coiling the mandrel is not required for all types of microtubing. In some instances microtubing with varied diameter and materials may provide a sufficient change in stiffness to be effective.

After braiding, the braided resin coated mandrel 29 is optionally passed over tank 19 with a suitable etching solution 81 (or alternatively a mechanical braid removal station). For steel wire or ribbon braid the preferred solution is a salt water solution through which electric current is passed to achieve electrochemical machining of the immersed braid. Controller 20 will selectively raise and lower dipping roller 21 to submerge selected portions of the resin coated mandrel 29 in the saline etching solution 81. The result is the selective removal of portions of the braid layer.

To mechanically remove a braid section, it is desirable that the braid to be removed consist of straight wires. Accordingly, the braid section on a length of microtubing would be likely to have a low pick count at the stiff proximal end, a high pick count at a more flexible distal portion, and straight wires (achieved by stopping the rotation of the carriers while continuing to pull wires with the capstan). A thin resin layer referred to as the braid matrix layer is then coated over the braid and,selectively removed by etching the areas where the straight wires are located. The straight wires can then be cut with wire cutters and fatigued to failure at the interface with the braid matrix layer. This process leaves relatively few irregularities such as wire burrs.

The braided resin coated mandrel 29 is then passed through another resin bath 22, curing oven 23 and optional tank 24 containing an etching solution and with controller 25 and dipping rod 26 for submerging selected portions of the composite coated mandrel 29. The resin layer encapsulating the braid is referred to as the braid matrix layer. By selected removal of portions of the initial matrix layer, and passing the resin coated mandrel 29 through another resin bath and curing oven, the braid can be encapsulated with different resins over predetermined lengths of microtubing. By using a relatively stiff material for the braid matrix at one end of a length of microtubing such as polyimide or PBAX grade NYLON, and a relatively flexible material such as FEP, PTFE or a low durometer polyurethane at the opposite end, the flexibility change over the length of the microtubing can be further enhanced.

One layer of resin cured material encasing the braid may be sufficiently thick to provide structural integrity to the resulting composite microtube, while still conforming generally to the texture of the outer surface of the woven braid. The exterior surface texture or roughness of such a composite microtube exhibits less drag when used as a guide catheter than a comparable smooth surfaced material. It will be understood that the mandrel 29 may also be coated with additional layers of resin at this stage before proceeding to the final step 27. Additional layers may create a smooth surfaced composite or provide additional thickness which can be ground smooth. In some instances, it is desirable to extrude the outer layer of the tubing. This is accomplished by passing the microtubing through an extruder, such as is used to manufacture thicker walled catheter tubing. It is also possible to vary the flexibility of the extruded layer by using a co-extruder that can switch between different materials over predetermined lenths of extrusion. With such a co-extrusion process a relatively high durometer material may be used for some segments and then transitioned to a relatively lower durometer to provide greater flexibility. Extruded layers would typically be used to provide additional wall thickness for the resulting microtubing, which has the effect of reducing the tendency of the tubing to kink. Extrusion may also be a more desirable process to use with some particular materials that are desirable for properties such as high flexibility, non-reactivity with respect to tissue, and non-thrombogenicity with respect to blood.

In the final step 27 the mandrel 29 and the composite tubing that coats the mandrel 29 are cut into desired lengths, the mandrel 29 is removed for recycling thereby defining a central lumen, and the resulting composite microtubing is cleaned and finished.

The traditional mandrel 29 is a wire of uniform diameter as illustrated in isolation in FIG. 1B. However, FIG. 1C illustrates a new mandrel 30 consisting of a continuous length of wire which has been manufactured or centerlessly ground to produce tapered segments a from wide point 31 to narrow point 32. Composite microtubes can be manufactured on these mandrels 30, the short segments b between narrow points 32 and wide points 31 being cut out and discarded, while the long segments a, have the mandrel removed for recycling, and are thereafter finished in the traditional manner. In this fashion, novel composite tapered microtubes can be manufactured in a continuous process.

In lieu of using tapered mandrels, it is also possible in some instances to produce tapered microtubes by heating and stretching selected portions of the microtubing. Typically this is accomplished by cutting the microtubing into segments, hanging the segments with a weight at one end, and heating portions of the microtubing segments, preferably with a tubular heater.

It will be understood that other mandrel shapes may also be desired. For instance, an elliptical or oval mandrel or a tapered oval mandrel might be used.

Figure 2:
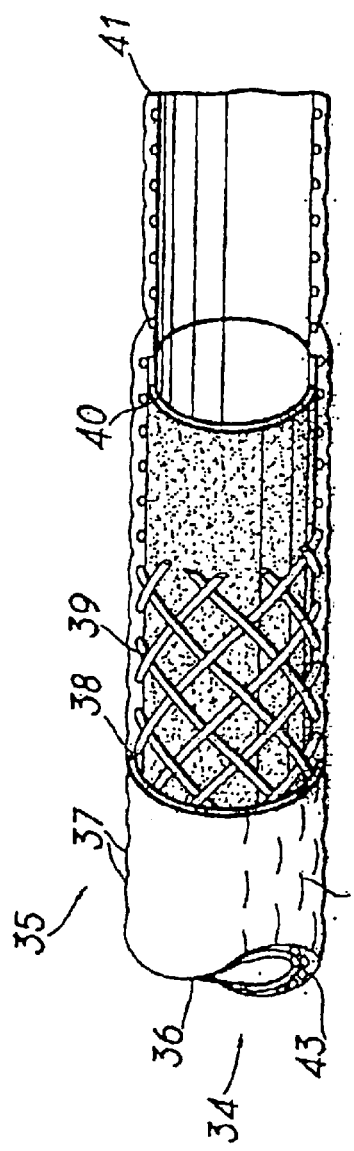
FIG. 2 is an enlarged partial side sectional view of a length of microtubing made according to the present invention in which the materials comprising the layers of the microtubing walls are varied over distance.

FIG. 2 illustrates an enlarged partial sectional view of a composite microtubing 35 according to the present invention. The proximate end 36 of the microtube 35 shows the exterior cured resin surface 42 of the microtube 35 conforming generally to the texture of the underlying wire braid, as shown by bumps 37. Wire 39 is in a cloth weave pattern and encased in the outer resin cured layer 38. Inner cured resin layer 40 is beneath the wire braid but has been removed at the distal end 41 of microtube 35. Accordingly, because the inner cured resin layer 40 is present in the proximate end 36 and removed at the distal end 41, the microtube 35 exhibits greater stiffness at its proximate end than at its distal end. Preferably inner cured resin layer 40 does not stop abruptly, but tapers off over about ¼ inch to 2 inches, and preferably about 1 inch, so that the flexibility of microtube 35 changes somewhat gradually and does not exhibit a heightened tendency to kink at the end of the inner cured resin layer 40. Cured resin layers 38, 40 and braid 38 define the composite wall 43, the inner surface of which defines lumen 34 extending axially through microtube 35.

Figure 3:
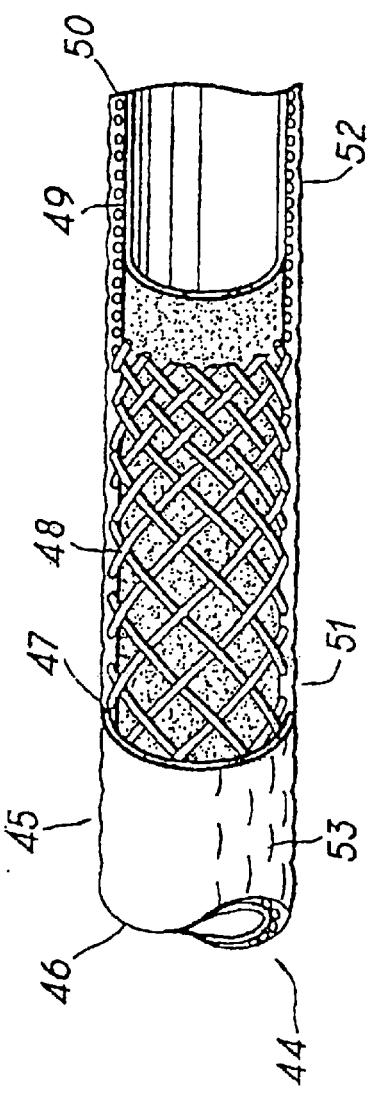
FIG. 3 is an enlarged partial side sectional view of a length of microtubing made according to the present invention with variable pick count braiding.

FIG. 3 illustrates an alternative microtube 45 according to the present invention. The proximate wall 46 of microtube 45 again shows an exterior cured resin surface 53 conforming generally to the texture of the underlying wire braid. The interior surface of wall 46 defines lumen 44 extending axially through microtube 45. Wires 48 are braided in a clothing weave varying from a relatively low pick count at position 51 to a relatively higher pick count at position 52. Wires 48 are embedded in outer cured resin layer 47. The wire braid is exterior of inner cured layer 49, which in this illustration proceeds the entire length of the microtube to distal end 50 of microtube 45. It has been discovered that increasing the pick count of the wire braid also increases the flexibility of the microtube. Accordingly, microtube 45 is relatively stiffer at proximate end 46 and position 51 where the pick count is relatively low, as contrasted with position 52 and the distal end 50 where the pick count is relatively high. An additional novel feature is that the pick count can be varied substantially, for instance from less than 50 picks per inch to 280 picks per inch when using 0.0015 inch diameter round steel wire braid, along a one inch segment of microtubing by using the wire guides described in FIG. 6. If the braid layer is replaced with coiled wire, ribbon, or fiber, similar variations in stiffness are achieved by altering the pitch of the coiling material with respect to the resin coated mandrel as it is wound. When the pitch approaches 90°, the greatest flexibility is achieved; when the pitch approaches 0°, the greatest stiffness is realized.

Figure 4:
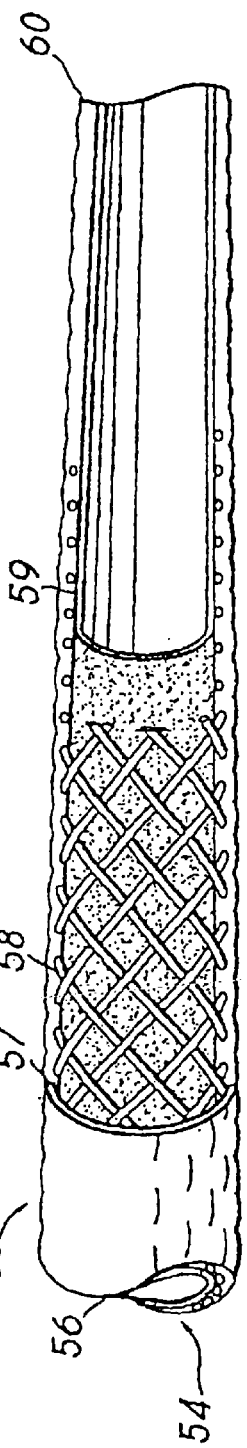
FIG. 4 is an enlarged partial side sectional view of a length of microtubing according to the present invention which is tapered and in which the braid layer is selectively removed.

FIG. 4 shows a tapered microtube 55 with the diameter of lumen 54 encompassed by proximate wall 56 being greater than the diameter encompassed distal wall 60. Also shown are inner cured resin layer 59, and wire 58 braided in a clothing weave and encased in outer cured resin layer 57. It has been established that stiffness varies proportionately to the third power of the diameter of a thin walled microtube and proportionately to the fourth power of the diameter of a thick walled tube. Accordingly, if the diameter of microtube 55 at proximate end 56 is twice the diameter at distal end 60, the proximate end 56 of microtube 55 will be approximately 8 times as stiff as distal end 60. It will be recognized that it is possible to combine a reduction in a microtube's diameter together with increasing the pick count of a wire braid layer, and etching away part or all of at least one layer of resin or braid from a portion of the microtube. In this fashion, a microtube construction is possible in which the proximate end is more than 100 times as stiff as the distal end, and the microtubing still provides satisfactory strength and resistance to kinking throughout.

Furthermore exotic variations are possible with other microtubing shapes. For instance, an elliptical or oval shaped microtube has greater flexibility in the direction of its minor axis and greater stiffness in the direction of its major axis. A tapered oval shape combines the characteristics of oval microtubing with the reduction in stiffness achieved by reducing the overall diameter of the microtubing.

FIG. 5 illustrates a microtubing 62 with a combination of the previously described techniques. Microtubing 62 has a proximate end 63 with interior diameter d and a smooth outer resin wall 64 encasing the woven wires 65, 68 which comprise a braid layer. The braided wires 65, 68 are woven over an inner resin layer 66 that commences at the proximate end 63 of the microtube 62 but which is etched or ground away as it approaches the distal end 67 of the microtube. In the illustrated embodiment, the etching has completely removed the inner resin layer 66 at the distal end 67. The pick count of the woven wires 65, 68 also varies, being relatively lower at the proximate end 63 and at wires 65 than at the distal end 67 and wires 68. The removal of inner resin layer 66 and the increased pick count toward the distal end 67 make the distal end 67 of the microtubing 62 more flexible than the proximate end 63. Adding further to the flexibility of the distal end 63 is that the distal inner diameter d' is approximately one half the proximal diameter d.

The changes in stiffness that can be realized with novel microtubings according to the present invention are exemplified by the samples tested in the following table:

TABLE I

| Distance From Proximal End (cm) | Inner Diameter (mm) | Outer Diameter (mm) | Picks/cm | Stiffness* gm/cm | Kink Diameter (cm) |
|---|---|---|---|---|---|
| Tube A - Inner layer polyimide, Stainless Steel braid .0015 inch diameter, Outer layer PTFE | | | | | |
| 5.1 | .757 | .965 | 14.2 | 117.7 | 3.17 |
| 20.3 | .757 | .965 | 17.3 | 118.0 | 3.17 |
| 35.6 | .757 | .968 | 18.1 | 82.3 | 2.54 |
| 50.8 | .759 | .975 | 22.0 | 56.2 | 1.27 |
| 66.0 | .759 | .978 | 22.8 | 42.8 | 1.02 |
| 81.3 | .762 | .978 | 26.8 | 37.7 | 1.02 |
| 91.4 | .765 | .996 | 52.8 | 21.2 | .51 |
| 111.8 | .765 | .996 | 56.7 | 23.1 | .51 |
| 127 | .765 | .993 | 53.5 | 26.0 | .51 |
| Tube B - Inner layer polyimide, Stainless Steel braid .0015 inch diameter, Outer layer PTFE | | | | | |
| 5.1 | .879 | 1.069 | 13.8 | 129.3 | 3.81 |
| 21.6 | .881 | 1.077 | 15.0 | 112.9 | 2.54 |
| 38.1 | .889 | 1.080 | 19.7 | 63.4 | 1.02 |
| 54.6 | .889 | 1.085 | 22.8 | 56.9 | 1.02 |
| 71.1 | .894 | 1.097 | 25.1 | 43.7 | .76 |
| 87.6 | .897 | 1.105 | 45.7 | 37.8 | .51 |
| 102.9 | .897 | 1.105 | 56.7 | 40.3 | .51 |
| Tube C - Inner layer PTFE, Second layer-polyimide (1), Stainless Steel braid .0015 inch diameter, Outer layer FEP | | | | | |
| 5.1 | .762 | 1.016 | 19.7 | 52.9 | 1.52 |
| 50.8 | .762 | 1.016 | 110.2 | 9.1 | .51 |
| Tube D - Inner layer polyimide, Stainless Steel Braid .0015 inch diameter Outer Layer FEP | | | | | |
| 5.1 | .867 | 1.041 | 19.7 | 41.26 | 1.52 |
| 50.8 | .635 | .867 | 110.2 | 17.68 | .51 |
| Tube E - Inner layer PTFE, second layer polyimide (1), stainless steel braid 0.0007 inches × 0.003 inches, outer layer Tecoflex 93A | | | | | |
| 5.1 | 0.711 | 0.94 | 15.7 | 128.8 | 1.27 |
| 114.3 | 0.711 | 0.889 | 52 | 4.3 | <0.3175 |

*Measured on a 1.27 cm (0.5 inch) segment centered at the specified distance from the proximal and.
(1) Second layer is removed by etching at about 40 cm from the proximal and FIG. 6 shows the braiding area 70 of a typical braiding machine, with resin coated mandrel 73 proceeding upward through pick down guide 71, and then being braided with wires 74 and proceeding through pick up guide 72. The braided resin coated mandrel 75 then proceeds to a take up reel or capstan. The braider is preferably controlled by a programmable logic chip so that the capstan speed, which controls the speed of the mandrel 73 through the braiding area, and the carrier speed, which controls the speed with which wire is braided or wrapped around the mandrel 73, can be altered when desired. Typically, a mandrel 73 will be either braided at a uniform rate, providing a braid layer with uniform pick count, or else at a variable rate repeating over a specified distance. The variable rate braided layer will have varied pick counts repeating over the specified distance. When the mandrel 73 has been completely processed so that all layers of braid and resin are finished, the mandrel 73 or tubing will be cut into lengths matching the specified distance and finished to provide microtubes with pick counts varying uniformly from the proximal end of each finished microtube. The resulting variable stiffness composite microtubes will each have the desired predetermined stiffness pattern varying over the length of those microtubes.

In the braiding areas, the wires being braided are at an angle α to the resin coated mandrel as they are wrapped. When the pick count increases, angle α increases. When the pick count decreases, angle α decreases. However, if the pick count of the braid is suddenly increased, up from say 45 to 90 picks per inch, the mere slowing of the capstan speed and increase of the carrier speed is not sufficient to immediately change the pick count. Instead, as angle α increases, the zone 76 in which the wires 74 contact the resin cured mandrel 73 moves higher and the full increase in pick count is only achieved gradually over about a one foot length. It is desired that more rapid pick count changes be realized for some tubing constructions. This result is achieved by the use of a pick-up guide 72 and a pick-down guide 71.

To keep the zone 76 at which wires 74 contact resin cured mandrel 73 relatively constant and thereby more rapidly achieve the full increase in pick count, pick-up guide 72 can be lowered to keep the wires 74 contacting mandrel 73 in zone 76. A similar problem occurs when the pick count is lowered. The pick-down guide 71 can be raised to keep the wires 74 contacting mandrel 73 in the same zone 76. Use of pick-up and pick-down guides allows significant pick count variations to be achieved over relatively short distances such as one inch (2.54 mm). It is not generally desirable to vary the pick count greatly over distances much shorter than one inch because of the increased tendency of the resulting microtubing to kink. The pick-up guide 72 and pick-down guide 71 achieve their desired results by changing the radius of the guide for the Steeger Braider from approximately 12 inches to the much smaller dimension of approximately 0.25 inches. Braider kinematics equations set forth in detail in "Processing Model of Circular Braiding," *Processing of Polymers and Polymeric Composites*, MD-V19, ASME 1990 by Guang Wu-Du, Peter Popper and Tsu-Wei Chen, show that conveyance length (the distance over which a pick count change is completed) due to a carrier or capstan speed change is minimized by making the guide radius as small as possible. Since by the use of the pick-up guide 72 and pick-down guide 71 rapid pick count changes can be achieved, near linear pick-count changes can also be achieved by changing either the capstan or carrier speeds in a linear fashion utilizing a programmable electronic controller.

FIG. 7 illustrates a microtubing 102 with only a single layer of cured resin 104. Microtubing 102 has a proximate end 103 with interior diameter d. Microtubing 102 narrows toward its distal end 107 to inner diameter d'. The cured resin layer 104 has also been etched toward the distal end 107 so that the thickness of the cured resin layer 104 is diminished.

FIG. 8 illustrates a multilayer microtubing 82 of uniform diameter. Microtubing 82 has a proximate end 83 and a distal end 87. Microtubing 82 is comprised of an inner resin cured layer 86 that commences at the proximate end 83 and extends to the distal end 87. Woven wires 85, 88 comprise a braid layer over the inner resin cured layer 86. The pick count of the woven wires 85, 88 also varies, being relatively lower at the proximate end 83 and at wires 88 than at the distal end 87 and wires 85. The intermediate resin cured layer 89 commences at the proximate end 83 of the microtube 82 and comprises the braid matrix layer at the proximate end 83, but is etched away as it approaches the distal end 87. An outer layer 84 proceeds the entire length of microtube 82 and comprises the braid matrix layer at the distal end 87 where the intermediate resin cured layer 89 was removed.

FIG. 9 illustrates a microtubing 92 with a combination of the previously described techniques and with outer extruded layer 91. Specifically, microtubing 92 has a proximate end 93 with interior diameter d and a smooth intermediate resin wall 94 encasing the woven wires 95, 98 which comprise a braid layer. The braided wires 95, 98 are woven over an inner resin layer 96 that commences at the proximate end 93 of the microtube 92 but which is etched or ground away as it approaches the distal end 97 of the microtube. In the illustrated embodiment, the etching has completely removed the inner resin layer 96 and the intermediate resin layer 99 toward the distal end. In addition, the pick count of the woven wires 95, 98 also varies being relatively lower at the proximate end 93 and wires 95, and increasing toward wires 98. The woven wires 95, 98 are completely removed either manually or preferably by electrochemical machining toward the distal end 97. The increased pick count towards the distal end 97 and complete removal of the wires 95, 98 at the distal end 97 makes microtubing 92 progressively more flexible toward the distal end 97. In addition, outer extruded layer 91 may be a soft and flexible material such as polyethylene or polyurethane. The removal of inner layer 96 and intermediate layer 99 toward the distal end 97 allows additional flexibility at the distal end 97 as does the reduced distal diameter d' relative to the proximal diameter d.

While the invention has been described in terms of its preferred embodiments, modifications obvious to one having ordinary skill in the art may be made without departing from the scope of the invention which are intended to be covered by the appended claims.

We claim:

1. A microtube having a proximal end and a distal end comprising:
   an inner cured resin layer;
   a braid layer over the inner cured resin layer;
   a medial cured resin layer over the braid layer wherein said medial layer extends from the proximal end of the microtube to a point intermediate the proximal end and the distal end at the microtube, encapsulating the braid and comprising a braid matrix layer between the proximal end and said intermediate point;
   a third layer over and encasing the medial layer between the proximal end and the intermediate point, said third layer also encapsulating the braid layer and comprising the remainder of the braid matrix layer.

2. The microtube of claim 1 wherein the braid layer is woven in a weave having relatively fewer picks per inch at the proximate end and relatively more picks per inch at the distal end.

3. The microtube of claim 1 wherein the braid layer extends from the proximate end of the microtube to a point between the intermediate point and the distal end.

4. The microtube of claim 1 wherein the inner cured resin layer is selected from the group consisting of polyimide and polytetrofluroethylene.

5. The microtube of claim 1 wherein the medial cured resin layer is comprised of polyimide.

6. The microtube of claim 1 wherein the inner cured resin layer, braid layer, intermediate cured resin layer and third cured resin layer comprise a composite tube wall of thickness less than 0.015 inches (0.381 mm).

7. The microtube of claim 2 having between 30 and 90 picks per inch at the proximal end and between 90 and 280 picks per inch at the distal end.

8. A microtube having a relatively stiff proximate end and a distal end and comprising:
   an inner cured resin layer;
   a braid layer over the inner cured resin layer from the proximate end to a point intermediate the proximate end and the distal end of the microtube; and
   an outer cured resin layer over and encasing the braid layer;
   wherein the braid is woven in a weave having relatively fewer picks per inch at the proximate end and relatively more picks per inch as it proceeds toward the intermediate point, such that said intermediate point is relatively more flexible than the proximate end.

9. A microtube having a tube wall with an outer surface and an inner lumen connecting a proximal end and a distal end, said tube wall comprising at least one cured resin layer and wherein the cross section of the inner lumen at the proximate end is of relatively greater area than the cross section of the inner lumen at the distal end; and wherein the thickness of the tube wall is relatively greater at the proximate end than at the distal end.

10. The microtube of claim 9 wherein the tube wall is comprised of at least one cured resin layer and at least one braid layer.

11. The microtube of claim 10 wherein at least one braid layer is comprised of a braid having relatively fewer picks per inch at the proximate end and relatively more picks per inch at the distal end.

12. The microtube of claim 9 wherein the tube wall at the distal end of the microtube has a thickness of less than 0.01 inch (0.254 mm).

13. A microtube having a proximate end and a distal end and comprising:
   an inner layer extending from the proximate end of the microtube to a point intermediate the proximate end and the distal end of the microtube; and
   a second layer extending from the proximate end to the distal end of the microtube.

14. The microtube of claim 13 wherein the inner layer is selected from the group consisting of cured resin and braid.

15. A microtube having a proximate end and a distal end and comprising:
   an inner cured resin layer extending between the proximate end and the distal end;
   a braid layer over the inner cured resin layer and extending from the proximate end of the microtube to a first point intermediate the proximate end and the distal end of the microtube;
   a second cured resin layer over the braid layer and extending from the proximate end to the distal end of the microtube; and
   an outer cured resin layer over and encasing the inner, braid and second cured resin layers.

16. A microtube having a proximal end and a distal end comprising:
   an inner cured resin layer extending between the proximate end and the distal end;
   a braid layer over the inner cured resin layer and extending from the proximate end of the microtube to a first point intermediate the proximate end and the distal end of the microtube;
   a second cured resin layer extending from the proximate end of the microtube to a second point intermediate the proximate end and the distal end of the microtube;
   and an outer cured resin layer over and encasing the inner, braid and second cured resin layers.

17. The microtube of claim 16 wherein said first point and said second point are the same.

18. A microtube having a proximal end and a distal end and comprising:
   an inner cured resin layer extending from the proximal end of the microtube to the distal end;

a second layer over the inner cured resin layer and extending from the proximal end of the microtube to a point intermediate the proximal end and the distal end of the microtube; and an outer cured resin layer over and encasing the inner and second layers, wherein the microtube is relatively stiff at its proximal end in comparison to the distal end.

19. A microtube having a proximal end and a distal end and comprising:

a braid layer woven in a weave having relatively fewer picks per inch at the proximal end and relatively more picks per inch at the distal end; and an outer cured resin layer over and encasing the braid layer, wherein the microtube is relatively stiff at the proximal end in comparison to the distal end.

20. The microtube of claim 8 wherein the inner cured resin layer is selected from the group consisting of polyimide and polytetrofluroethylene.

21. The microtube of claim 8 wherein the outer cured resin layer is comprised of polyimide.

22. The microtube of claim 4 wherein the inner cured resin layer, braid layer, and outer cured resin layer comprise a composite tube wall of thickness less than 0.015 inches (0.381 mm).

23. The microtube of claim 8 having between 30 and 90 picks per inch at the proximal end and between 90 and 280 picks per inch at the intermediate point.

* * * * *